United States Patent
Liran et al.

(10) Patent No.: US 10,555,837 B2
(45) Date of Patent: Feb. 11, 2020

(54) INTRAOCULAR PROSTHESIS

(71) Applicant: RAINBOW MEDICAL LTD., Herzliya (IL)

(72) Inventors: Tuvia Liran, Qiryat Tivon (IL); Yossi Gross, Moshav Mazor (IL)

(73) Assignee: RAINBOW MEDICAL LTD., Herzliya (IL)

( * ) Notice: Subject to any disclaimer, the term of this patent is extended or adjusted under 35 U.S.C. 154(b) by 225 days.

(21) Appl. No.: 15/262,536

(22) Filed: Sep. 12, 2016

(65) Prior Publication Data

US 2018/0071146 A1 Mar. 15, 2018

(51) Int. Cl.
*A61F 2/16* (2006.01)
*A61F 9/08* (2006.01)
*G02C 11/00* (2006.01)

(52) U.S. Cl.
CPC .............. *A61F 9/08* (2013.01); *A61F 2/16* (2013.01); *G02C 11/10* (2013.01); *A61F 2002/1683* (2013.01); *A61F 2250/0002* (2013.01)

(58) Field of Classification Search
CPC ............... A61F 2/16; A61F 2002/1683; A61F 2250/0002; G02C 11/10
See application file for complete search history.

(56) References Cited

U.S. PATENT DOCUMENTS

| | | | |
|---|---|---|---|
| 3,996,627 A | 12/1976 | Deeg et al. | |
| 5,653,751 A | 8/1997 | Samiy et al. | |
| 7,001,427 B2 * | 2/2006 | Aharoni | A61F 9/08 623/4.1 |
| 7,736,390 B2 | 6/2010 | Aharoni et al. | |
| 7,776,087 B2 | 8/2010 | Aharoni et al. | |
| 7,918,886 B2 | 4/2011 | Aharoni et al. | |
| 8,197,539 B2 | 6/2012 | Nasiatka et al. | |
| 2012/0259410 A1 * | 10/2012 | Gefen | A61F 2/14 623/6.11 |
| 2016/0310325 A1 | 10/2016 | Jiao et al. | |
| 2018/0367769 A1 | 12/2018 | Greenberg | |

FOREIGN PATENT DOCUMENTS

WO 2006/015315 2/2006

* cited by examiner

*Primary Examiner* — David H Willse
*Assistant Examiner* — Tiffany P Shipmon
(74) *Attorney, Agent, or Firm* — Sughrue Mion, PLLC

(57) ABSTRACT

Intraocular apparatus is provided, having an anterior side and a posterior side, and configured for use with an extraocular imaging device. The intraocular apparatus includes a photovoltaic energy receiver, or an RF energy receiver, on the anterior side which receives energy from outside the eye to power the intraocular apparatus. Additionally, the intraocular apparatus includes a photodiode on the anterior side of the intraocular apparatus which receives data from the extraocular imaging device. An application-specific-integrated-circuit (ASIC) is positioned on the posterior side of the intraocular apparatus and includes (i) circuitry configured to process the data from the photodiode into an image, (ii) an electronic display, e.g., a light-emitting diode (LED) display, which emits light representing the image, and (iii) at least two through-silicon vias connecting the ASIC to the photovoltaic energy receiver and to the photodiode. Other applications are also described.

11 Claims, 8 Drawing Sheets

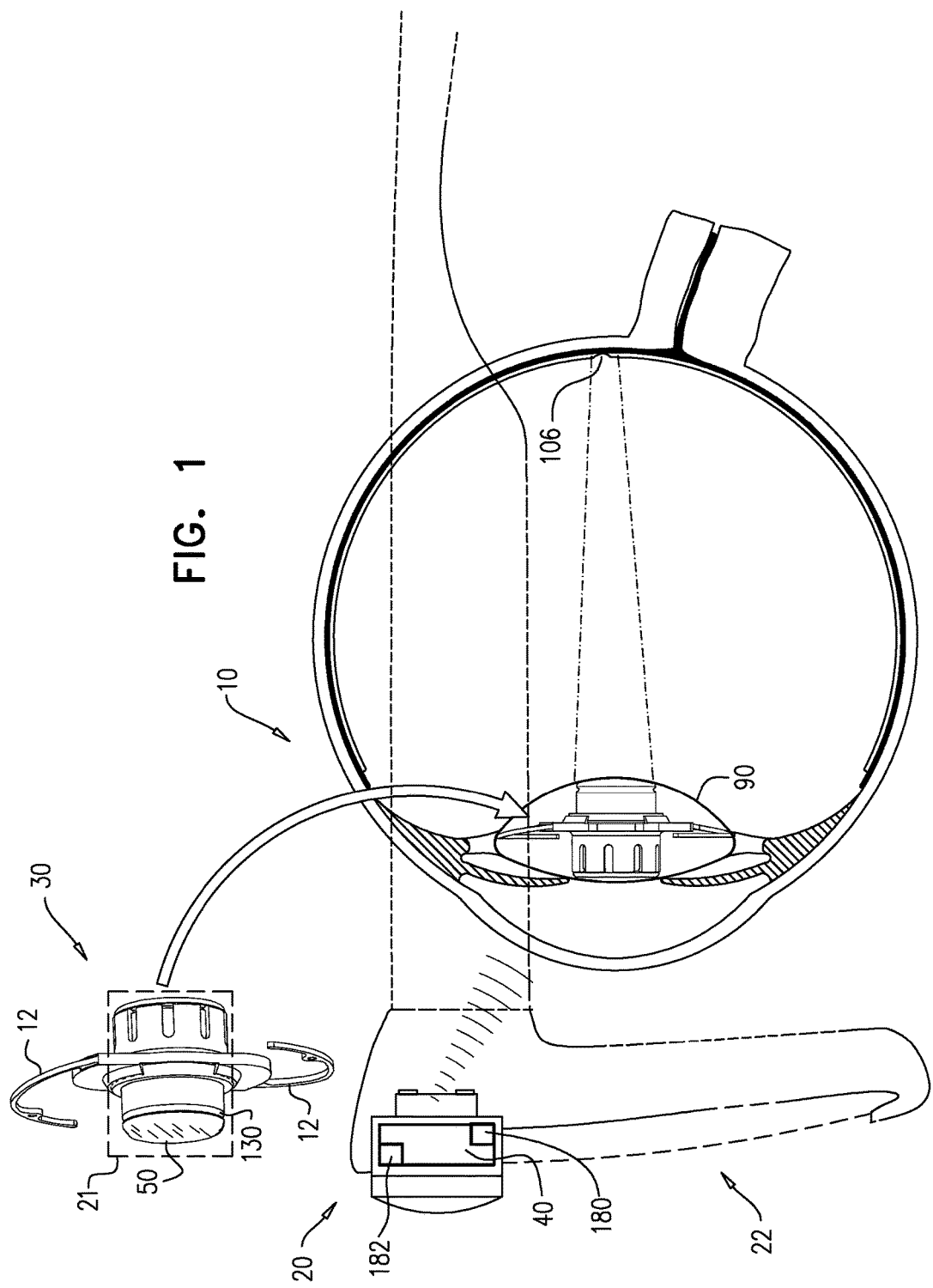

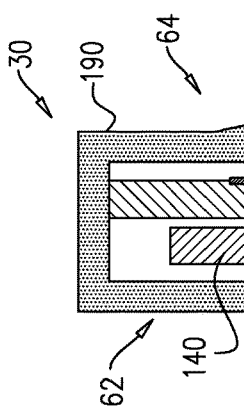
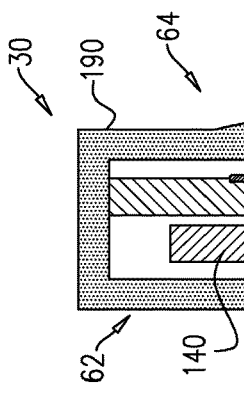
FIG. 2A
FIG. 2B

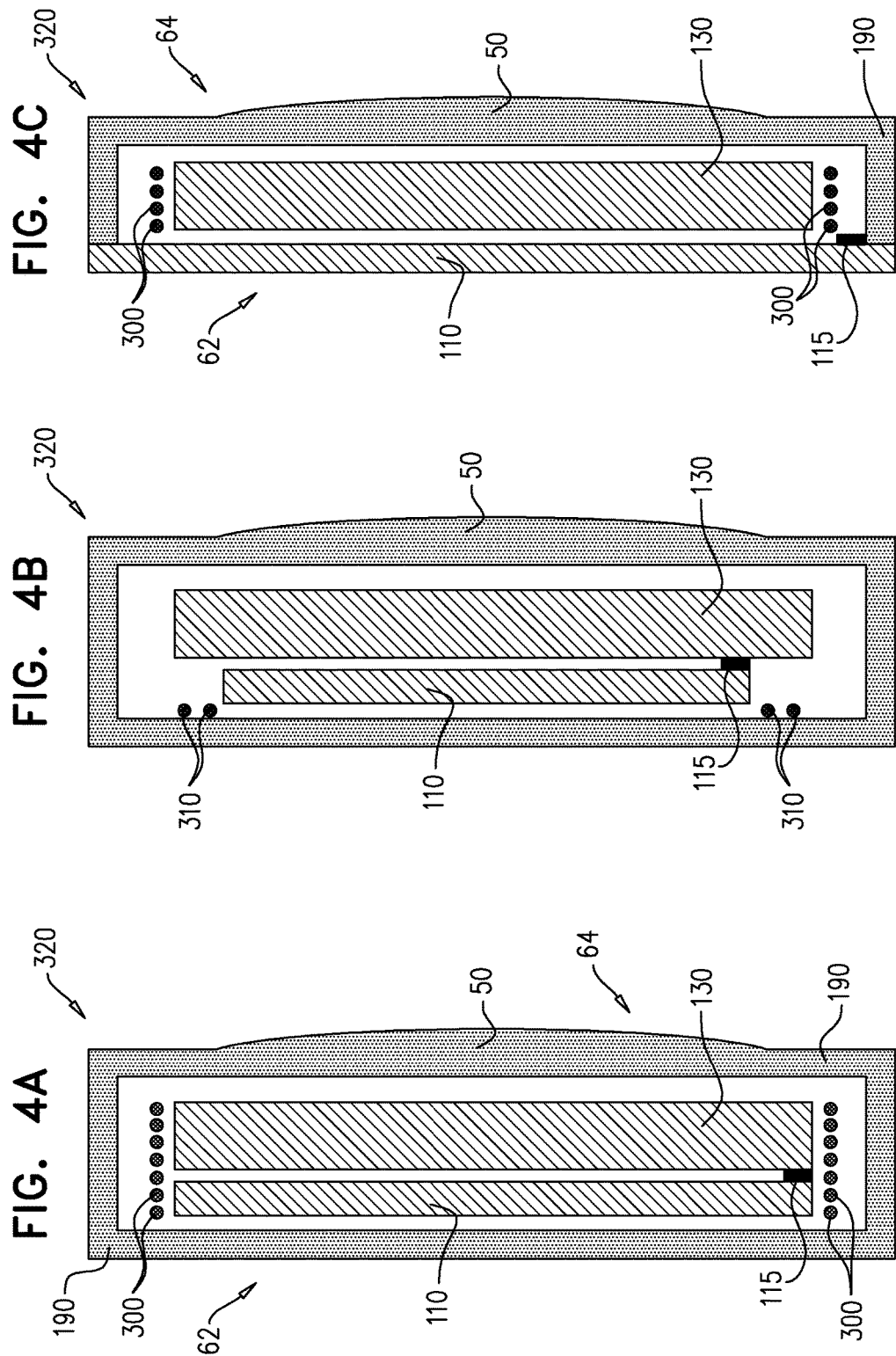

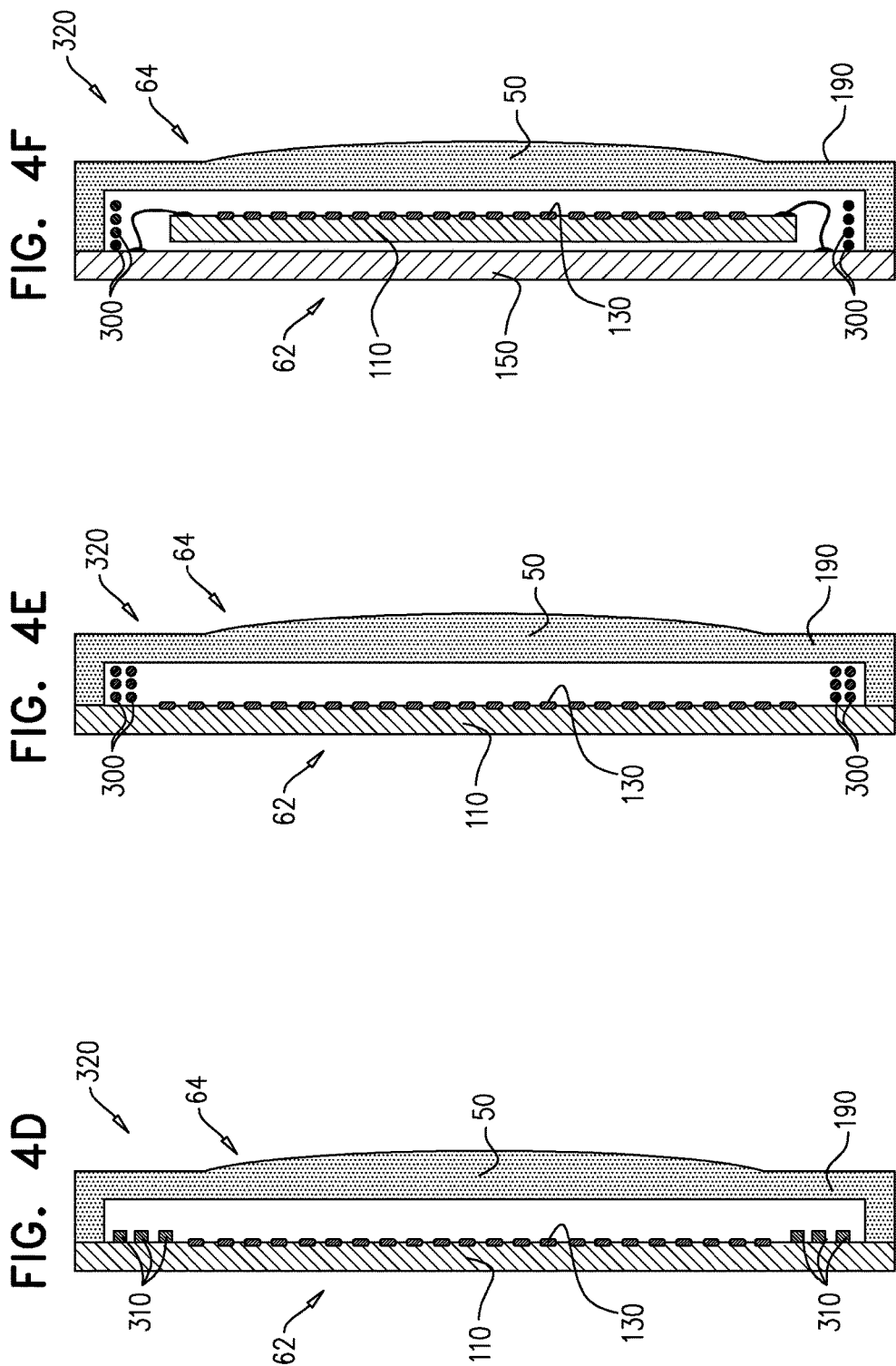

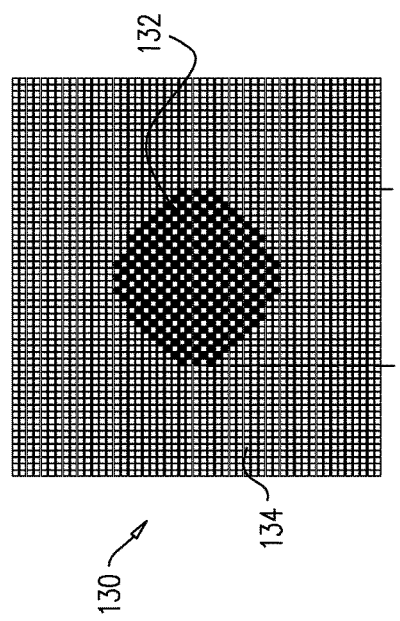
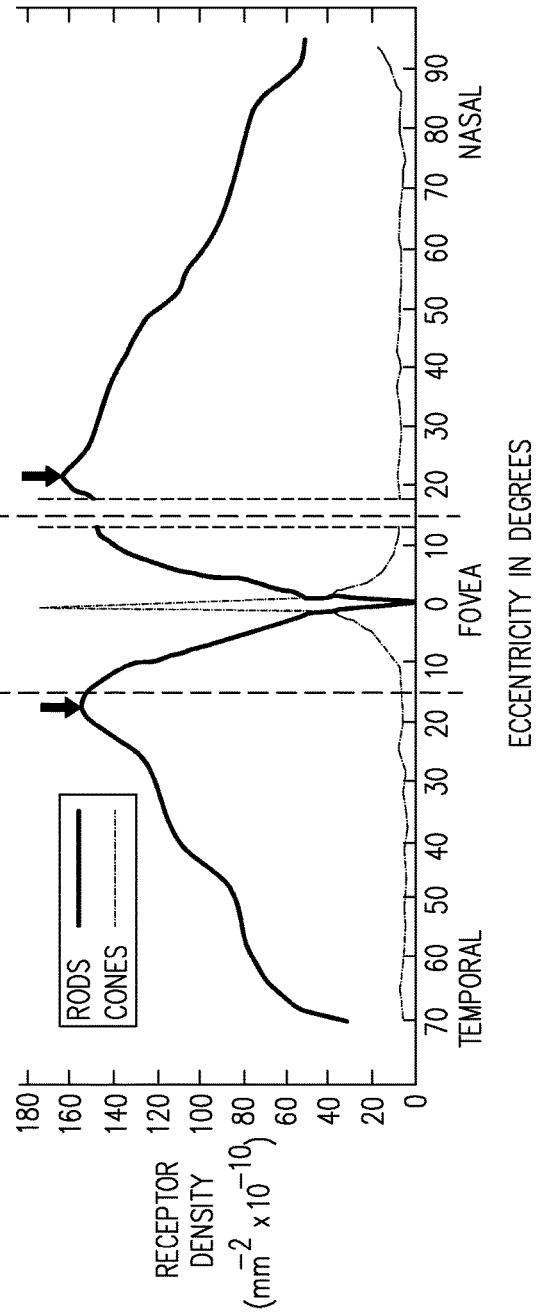
FIG. 6

INTRAOCULAR PROSTHESIS

FIELD OF THE INVENTION

The present invention relates generally to implantable medical devices, and specifically to an intraocular implant.

BACKGROUND

The cornea is a transparent, dome-shaped outermost layer of the eye. The cornea covers, the iris and the pupil and plays a role in protecting the eye from germs, dust, and other harmful matter. The cornea additionally functions to focus vision, typically contributing to more than 50 percent of the eye's total focusing power. Light that passes through the cornea is refracted onto the lens of the eye and further focused by the lens onto the retina. Thus, a healthy cornea is typically clear and transparent to allow passing of light there through. Corneal opacities can cause vision impairment and blindness.

U.S. Pat. No. 7,736,390 to Aharoni describes an artificial vision system including a sealed capsule adapted for intraocular placement upstream of a retina, an electronic display located within the sealed capsule and focusing optics located within the sealed capsule and arranged for focusing an image on the electronic display onto the retina.

U.S. Pat. No. 5,653,751 to Samiy describes apparatus and methods that project images onto the retina of an eye. The apparatus can include an image memory element for storing an image signal representative of a visual image, a projection element in an electrical circuit with the image memory element for generating an optical image signal of the type suitable for detection by a retina and being representative of the visual image, and a focus element that is adapted for implantation into the eye at a position in the eye which is posterior to the cornea and anterior to the retina and that is optically coupled to the projection element for focusing the optical image onto the retina. The projection element can include a display device that is dimensionally adapted for disposition within the eye at a position posterior to the cornea. The display device can be a liquid crystal display element that has an illuminator element optically coupled to the display device or alternatively can include a laser diode element that optically couples to a scanning mirror that projects light through a damaged cornea.

SUMMARY OF THE INVENTION

Some applications of the present invention provide intraocular apparatus for providing at least partial vision in a subject suffering from a corneal disease. Typically, the intraocular apparatus is used in combination with an extraocular imaging device that captures an image that is in turn displayed by the intraocular apparatus onto the retina of the subject, thereby providing vision to the subject.

In accordance with some applications of the present invention, the intraocular apparatus is encapsulated e.g., within a glass encapsulation, and is shaped and sized to be implanted in an anterior segment of the eye, typically, in a capsular bag of the eye.

For some applications, the intraocular apparatus comprises a photovoltaic energy receiver on an anterior side of the intraocular apparatus, the photovoltaic energy receiver being configured to receive energy from outside the eye and to power the intraocular apparatus. Typically, the photovoltaic energy receiver receives infrared light from an external light, source, e.g., a laser, and converts the received energy from the laser into electrical energy for powering the intraocular apparatus. Typically, the cornea is opaque and therefore not transparent to visible light. However, some residual transparency of the cornea to infrared light exists. The photovoltaic energy receiver is typically configured to absorb the IR light.

Additionally, the intraocular apparatus typically comprises a photodiode on the anterior side of the intraocular apparatus, and circuitry and an electronic display both positioned on an application-specific-integrated-circuit (ASIC) (or a dedicated display microchip), on posterior side of the intraocular device.

The photodiode typically receives data from the extraocular imaging device, and the circuitry processes the data from the photodiode into an image. The electronic display, typically a light-emitting diode (LED) display, emits light representing the image, such that the image is displayed onto the retina. For some applications, least two through-silicon vias connect the ASIC to the photovoltaic energy receiver and to the photodiode. Typically, the intraocular apparatus further comprises a lens positioned posterior to the LED display and configured to focus the image onto the retina.

For some applications, the LED display comprises a central polychrome portion. (e.g., showing red and green, or showing red, green, and blue) and a peripheral monochrome portion (e.g., "black and white") which may be implemented with any single color, surrounding the central portion.

There is therefore provided in accordance with some applications of the present invention, intraocular apparatus (i) shaped and sized to be implanted entirely in a subject's eye, (ii) having an anterior side and a posterior side, and (iii) configured for use with an extraocular imaging device, the intraocular apparatus including:

a photovoltaic energy receiver on the anterior side of the intraocular apparatus configured to receive energy from outside the eye and to power the intraocular apparatus;

a photodiode on the anterior side of the intraocular apparatus configured to receive data from the extraocular imaging device;

an application-specific-integrated-circuit (ASIC) on the posterior side of the intraocular apparatus including (i) circuitry configured to process the data from the photodiode into an image, (ii) an electronic display configured to emit light representing the image, and (iii) at least two through-silicon vias connecting the ASIC to the photovoltaic energy receiver and to the photodiode.

For some applications, the apparatus further includes a lens posterior to the ASIC, configured to focus the light emitted by the electronic display onto a retina of the subject.

For some applications, the intraocular apparatus is shaped and sized to be implanted in a capsular bag of the subject.

For some applications, the apparatus further includes an encapsulation, at least partially including glass, the encapsulation configured to encapsulate the photovoltaic energy receiver, the photodiode, and the ASIC.

For some applications, a posterior side of the encapsulation forms a lens configured to focus the light emitted by the electronic display onto a retina of the subject.

For some applications, the at least two through-silicon vias include exactly three through-silicon vias.

For some applications, the at least two through-silicon vias include exactly four through-silicon vias.

For some applications, the apparatus further includes an eye-tracking sensor configured to sense a position of the subject's eye and to generate a signal in response thereto, and in response to the signal, the electronic display is configured to emit light representing an image corresponding to the position of the subject's eye sensed by the eye-tracking sensor.

For some applications, the extraocular imaging device is configured to change a view captured by the extraocular imaging device in response to the signal.

For some applications, the electronic display includes a light-emitting diode (LED) display.

There is further provided in accordance with some applications of the present invention, intraocular apparatus (i) shaped and sized to be implanted entirely in a subject's eye, and (ii) configured for use with an extraocular imaging device, the intraocular apparatus including:

an energy receiver configured to receive energy from outside the eye and to power the intraocular apparatus;

a data receiver configured to receive data from the extraocular imaging device;

circuitry configured to process the data from the data receiver into an image;

an electronic display configured to emit light representing the image; and an encapsulation (i) configured to fully encapsulate the energy receiver, the data receiver, the circuitry, and the electronic display, and (ii) forming a lens on a posterior side of the encapsulation, the lens configured to focus the light emitted by the electronic display onto a retina of the subject.

For some applications, the energy receiver includes a photovoltaic energy receiver, and the data receiver includes a photodiode.

For some applications, the apparatus includes at least two through-silicon vias connecting:

(a) the electronic display and the circuitry, to
(b) the data receiver and the energy receiver.

For some applications, the energy receiver includes a radiofrequency (RF) power receiving coil, and the data receiver includes a radiofrequency (RF) data receiver.

There is further provided in accordance with some applications of the present invention, intraocular apparatus shaped and sized to be implanted entirely in the subject's eye and configured for use with an extraocular imaging device, the intraocular apparatus including:

an electronic display including:
a central polychrome portion; and
a peripheral monochrome portion, surrounding the central portion,
the electronic display being configured to emit light representing an image received by the imaging device.

For some applications, the electronic display includes a light-emitting diode (LED) display.

There is further provided in accordance with some applications of the present invention, intraocular apparatus shaped and sized to be implanted entirely in a subject's eye and configured for use with an extraocular imaging device, the intraocular apparatus including:

an electronic display including:
a central portion; and
a peripheral portion, surrounding the central portion,
the peripheral portion having resolution that is higher than a resolution of the central portion.

For some applications, the electronic display includes a light-emitting diode (LED) display.

For some applications, the central portion includes a polychrome portion; and the peripheral portion includes a monochrome portion.

There is further provided in accordance with some applications of the present invention, intraocular apparatus (i) shaped and sized to be implanted entirely in a subject's eye, and (ii) configured for use with an extraocular imaging device, the intraocular apparatus including:

an energy receiver configured to receive energy outside the eye and to power the intraocular apparatus;

a data receiver configured to receive image data from the extraocular imaging device;

circuitry configured to process the data received by the data receiver into an image, an electronic display configured to emit light representing the image; and an eye-tracking sensor configured to sense a position of the subject's eye and to generate a signal in response thereto, the electronic display being, configured to emit light representing a portion of the image corresponding to the position of the subject's eye sensed by the eye-tracking sensor.

For some applications, in response to the signal generated by the eye-tracking sensor, the circuitry changes the image captured by the extraocular imaging device such that the portion of the image corresponding to the position of the subject's eye, as sensed by the eye-tracking sensor, is displayed onto the electronic display.

For some applications, the extraocular device is configured to change a view captured by the extraocular imaging device in response to the signal.

There is further provided in accordance with some applications of the present invention, an extraocular device for use with an intraocular apparatus configured to display an image onto a retina of a subject, the extraocular device including:

a camera configured to capture the image; and an eye-tracking sensor coupled to the camera and configured to sense a position of the subject's eye and to generate a signal in response thereto such that in response to the signal, the intraocular apparatus d splays onto the retina a portion of image corresponding to the position of the subject's eye as sensed by the eye-tracking sensor.

For some applications, the extraocular device is a component in a vision system and the vision system additionally includes the intraocular apparatus, including:

an energy receiver configured to receive energy from outside the eye and to power the intraocular apparatus;

a data receiver configured to receive image data from the extraocular imaging device;

circuitry configured to process the data received by the data receiver into the image, an electronic display configured to emit light representing the image.

For some applications, the extraocular device is configured to change a view captured by the extraocular imaging device in response to the signal.

The present invention will be more fully understood from the following detailed description of applications thereof, taken together with the drawings, in which:

BRIEF DESCRIPTION OF THE DRAWINGS

FIG. 1 is a schematic illustration of vision system comprising intraocular apparatus for use with an extraocular imaging device, in accordance with some applications of the present invention;

FIGS. 2A and 2B are schematic illustrations of components of the intraocular apparatus in accordance with some applications of the present invention;

FIGS. 4A, 4B, 4C, 4D, 4E and 4F are schematic illustrations of additional configurations of the intraocular apparatus in accordance with some applications of the present invention;

FIG. 6 is a graph showing the intraocular display of FIGS. 5A and 5B, with respect to a fovea of the subject, in accordance with some applications of the present invention.

DETAILED DESCRIPTION OF EMBODIMENTS

Figure 3:
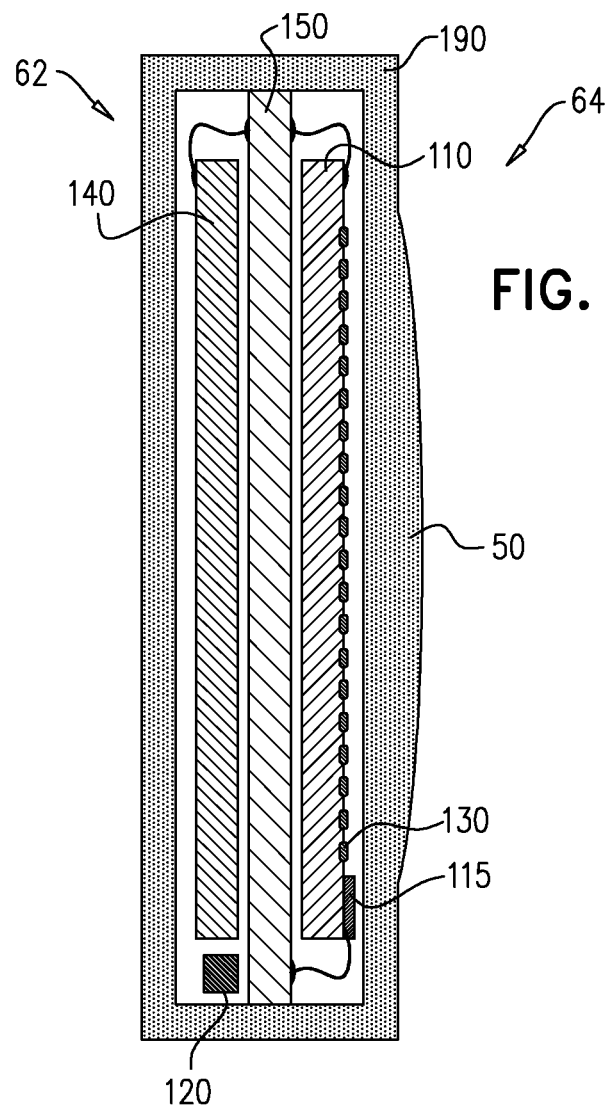
FIG. 3 is a schematic illustration of components of the intraocular apparatus in accordance with some applications of the present invention.

Reference is made to FIG. 1, which is a schematic illustration showing a vision system 20 comprising intraocular apparatus 30 for use with an extraocular imaging device 40 such as a camera, in accordance with some applications of the present invention.

Extraocular imaging device 40 is coupled to a mount 22 that is placed in front of an eye 10 of the subject. Mount 22 typically comprises a pair of eyeglasses worn by the subject. Extraocular imaging device 40 captures an image, and transmits data representing that image to the intraocular apparatus.

Intraocular apparatus 30 typically comprises an implant which includes an encapsulated optics and electronics portion disposed within a central portion 21 of the implant, the implant being shaped and sized to be implanted in a capsular bag 90 of eye 10, following removal of a lens of the subject (as shown in FIG. 1). For some applications, intraocular apparatus 30 comprises at least one, e.g., two fixation loops 12 configured to anchor apparatus 30 to capsular bag 90. Typically, central portion 21 of intraocular apparatus 30 is fully encapsulated in a bio-compatible hermetic encapsulation 190 (shown in FIGS. 2A-B), e.g., a glass encapsulation, or a combined glass and silicon encapsulation. For such a combined glass and encapsulation, it is noted that the encapsulation surrounding light-receiving and/or light-transmitting portions of intraocular apparatus 30, is a transparent glass encapsulation.

The data transmitted by extraocular imaging device 40 is received by intraocular apparatus 30 and displayed as an image onto a retina 106 of the subject, providing the subject with vision of the image. For some applications, intraocular apparatus 30 further comprises a lens 50 that focuses the image onto retina 106.

Reference is now made to FIGS. 2A-B and 3, which are schematic illustrations of the components of intraocular apparatus 30, in accordance with respective applications of the present invention. Intraocular apparatus 30 is typically shaped to define an anterior side 62 and a posterior side 64. When implanted in eye 10 of the subject, anterior side 62 is positioned to face an iris of the eye, and posterior side 64 is positioned to face the posterior segment of eye 10.

For some applications, intraocular apparatus 30 receives power and data by infrared (IR) light from a laser or LED light source. Intraocular apparatus 30 typically comprises a photovoltaic energy receiver 140 on anterior side 62 of intraocular apparatus 30. Photovoltaic energy receiver 140 is configured to receive energy from outside the eye, and to power intraocular apparatus 30. Typically, the photovoltaic energy receiver receives infrared light from an external light source, e.g., from a laser or LED coupled to mount 22, and converts the energy received from the light into electrical energy for powering intraocular apparatus 30.

Additionally, intraocular apparatus 30 typically comprises a photodiode 120 on anterior side 62. Photodiode 120 typically receives, in a wireless manner, image data from extraocular imaging device 40. Additionally, extraocular imaging device 40 may transmit configuration data, in addition to the image data. The configuration data may include, for example, display parameters, such as brightness, magnification, or various color settings. The configuration data may also change the configuration of a processor in intraocular apparatus 30 or enable changes n the format of the image data being transferred.

Posterior side 64 of intraocular apparatus 30 typically comprises an application-specific-integrated-circuit (ASIC) 110. ASIC 110 comprises circuitry 115 which processes the data from photodiode 120 into an image. ASIC 110 additionally comprises an electronic display 130, e.g., a micro-light-emitting diode (LED) display, which emits light representing the image, such that the image is displayed onto the retina. Individual LEDs of display 130 are shown in FIGS. 2A-B and 3 not to scale; typically, display 130 comprises thousands, tens of thousands, or hundreds of thousands of individual LEDs.

Typically, at least two through-silicon vias 170 are provided to connect ASIC 110 to photovoltaic energy receiver 140 and to photodiode 120. As shown in FIG. 2A, for some applications, ASIC 110 is shaped to define four through-silicon vias 170 for connecting ASIC 110 to photovoltaic energy receiver 140 and to photodiode 120. For other applications, ASIC 110 is shaped to define three through-silicon vias 170 for connecting ASIC 110 to photovoltaic energy receiver 140 and to photodiode 120, as shown in FIG. 2B. It is noted that for some applications (not shown) ASIC 110 is shaped to define fewer than three or more than four through-silicon vias 170. Thus, ASIC 110 may be connected to photovoltaic energy receiver 140 and to photodiode 120 by at least three or at least four through-silicon vias 170, and/or fewer than 20 through-silicon vias 170 (e.g., fewer than ten through-silicon vias 170).

Alternatively or additionally, an interposer 150 connects ASIC 110 and photovoltaic energy receiver 140, as shown in FIG. 3. For some applications, interposer 150 is shaped to define vias 170 (e.g., two or more vias) for connecting ASIC 110 to photovoltaic energy receiver 140 and to photodiode 120 (vias not shown). In 150 may comprise glass, silicon, ceramic or any other suitable substrate known in the art.

Electronic display 130 typically comprises a micro-LED display having a resolution of at least 50,000 and/or less than 1,000,000 pixels, typically with a pitch of at least 8 microns and/or less than 25 microns. For example, the light-emitting-diodes are positioned on ASIC 110 using pick-and-place technology, or transfer-printed technology. The pixels of display 130 may cover over 50% of the area of ASIC 110. Use of non-organic LEDs in electronic display 130 typically contributes to display 130 having low outgassing.

It is noted that for some applications electronic display 130 comprises a LCD (Liquid Crystal Display), a LCOS (Liquid Crystal on Silicon), an OLED (Organic Light Emitting diode), a micro OLED, a scanning mirror, and/or DLP (Digital Light Processing).

As shown, intraocular apparatus 30 additionally comprises lens 50 that focuses, onto retina 106, the light representing the image that is emitted by electronic display 130. For some applications, encapsulation 190 forms lens 50. In other words, lens 50 is not a separate component which is coupled to encapsulation. 190, but rather, at least a portion of a posterior side of encapsulation 190, has the properties of a focussing lens.

Reference now made to FIGS. 4A-B. For some applications, vision system 20 comprises intraocular apparatus 320 for use with an extraocular imaging device 40 such as a camera, in accordance with some applications of the present invention. Intraocular apparatus 320 is generally the same as intraocular apparatus 30 except for when indicated otherwise.

Intraocular apparatus 320 is typically shaped to define an anterior side 62 and a posterior side 64. When implanted in eye of the subject, anterior side 62 is positioned to face an iris of the eye, and posterior side 64 is positioned to face the posterior segment of eye 10.

Typically, intraocular apparatus 320 receives power and data by radiofrequency (RF) from an extraocular RF transmitting coil which is typically coupled to mount 22 and powered by a battery. As shown in FIG. 4A, intraocular apparatus 320 typically comprises an RF receiving coil 300 which receives power from the extraocular RF transmitting coil, to power intraocular apparatus 320. Typically, the extraocular RF transmitting coil also transmits image data, based on data acquired by imaging device 40, to RF receiving coil 300. RF receiving coil 300 receives the image data from the extraocular RF transmitting coil. The image data are typically processed by an RF data receiver in intraocular apparatus 320.

Intraocular apparatus 320 typically comprises an application-specific-integrated-circuit (ASIC) 110 (or a dedicated display microchip). ASIC 110 comprises circuitry 115 which processes the data from RF receiving coil 300 to form an image. On posterior side 64, intraocular apparatus 320 comprises an electronic display 130, e.g., a micro-light-emitting diode (LED) display, which emits light representing the image, such that the image is projected onto the retina. It is noted that although display 130 and ASIC 110 are shown as separate components, for some applications, display 130 is integrated into a posterior side of ASIC 110.

For some applications, intraocular apparatus 320 comprises a printed RF receiving coil 310 as shown in FIG. 4B. For some applications, coil 310 is formed as part of ASIC 110, as shown FIG. 4D.

Reference is now made to FIG. 4C-F. For some applications, intraocular apparatus 320 is encapsulated partly by ASIC 110, or by interposer 150, and not fully encapsulated by encapsulation 190. As shown in FIGS. 4C-E, for some applications, ASIC 110 encapsulates anterior side 62 of intraocular apparatus 320 and is attached to encapsulation 190. For other applications, interposer 150 encapsulates anterior side 62 of intraocular apparatus 320, as shown in FIG. 4F.

Reference is made to FIGS. 2A-4F. It is noted that image data and/or configuration data may be transferred from extraocular imaging device 40 to intraocular apparatus 30 and/or 320 using IR and/or RF protocols known in the art, or other protocols. For example, for some applications the intraocular apparatus is powered by infrared light (IR) and image data are received For other applications, the intraocular apparatus is powered by RF and data are received by IR.

Reference is again made to FIG. 1. For some applications, vision system 20 is configured to modify the image which is displayed on electronic display 130 based on a direction of the subject's gaze. For some applications, vision system 20 comprises an eye-tracking sensor 180. For some applications, sensor 180 is coupled to imaging device 40 as shown in FIG. 1. Alternatively, sensor 180 can be coupled to (e.g., incorporated in) intraocular apparatus 30 or 320, as shown for example in FIG. 2B.

Typically, eye-tracking sensor 180 senses a position, e.g., an angle, of eye 10 and in response to the sensing, generates a signal which is sent to extraocular imaging device 40 or to circuitry coupled to extraocular imaging device 40. As appropriate, eye-tracking techniques known in the art may be used. Extraocular imaging device 40, in turn, may change a view it captures to correspond to the view to which eye 10 is directed. For some such applications, a motor element 182 moves extraocular imaging device 40 such that device 40 captures the view to which eye 10 is directed.

Alternatively, extraocular imaging device 40 generally always captures a large view by having a wide-angle lens (e.g., by having a fish-eye lens), but in response to the signal from eye-tracking sensor 180, only a portion of the full view (i.e., a portion of the view corresponding to the subject's gaze) is displayed onto electronic display 130.

For some applications, the signal from eye-tracking sensor 180 is sent to extraocular imaging device 40 or to circuitry coupled to extraocular imaging device 40. In response to the signal, circuitry coupled to extraocular imaging device 40 changes a portion of the view that is displayed on electronic display 130, to correspond to the subject's gaze.

For some applications, the signal from eye-tracking sensor 180 is sent to circuitry 115 of intraocular apparatus 30, instead of or in addition to the signal being sent to extraocular imaging device 40 or to the circuitry coupled to extraocular imaging device 40. In response to the signal, circuitry 115 changes a portion of the view that is displayed onto electronic display 130 corresponding to the subject's gaze.

Typically, displaying an image in accordance with movement of eye 10 generally reduces the need for the subject to move his head in order for imaging device 40 to capture a desired scene.

Figure 5A:
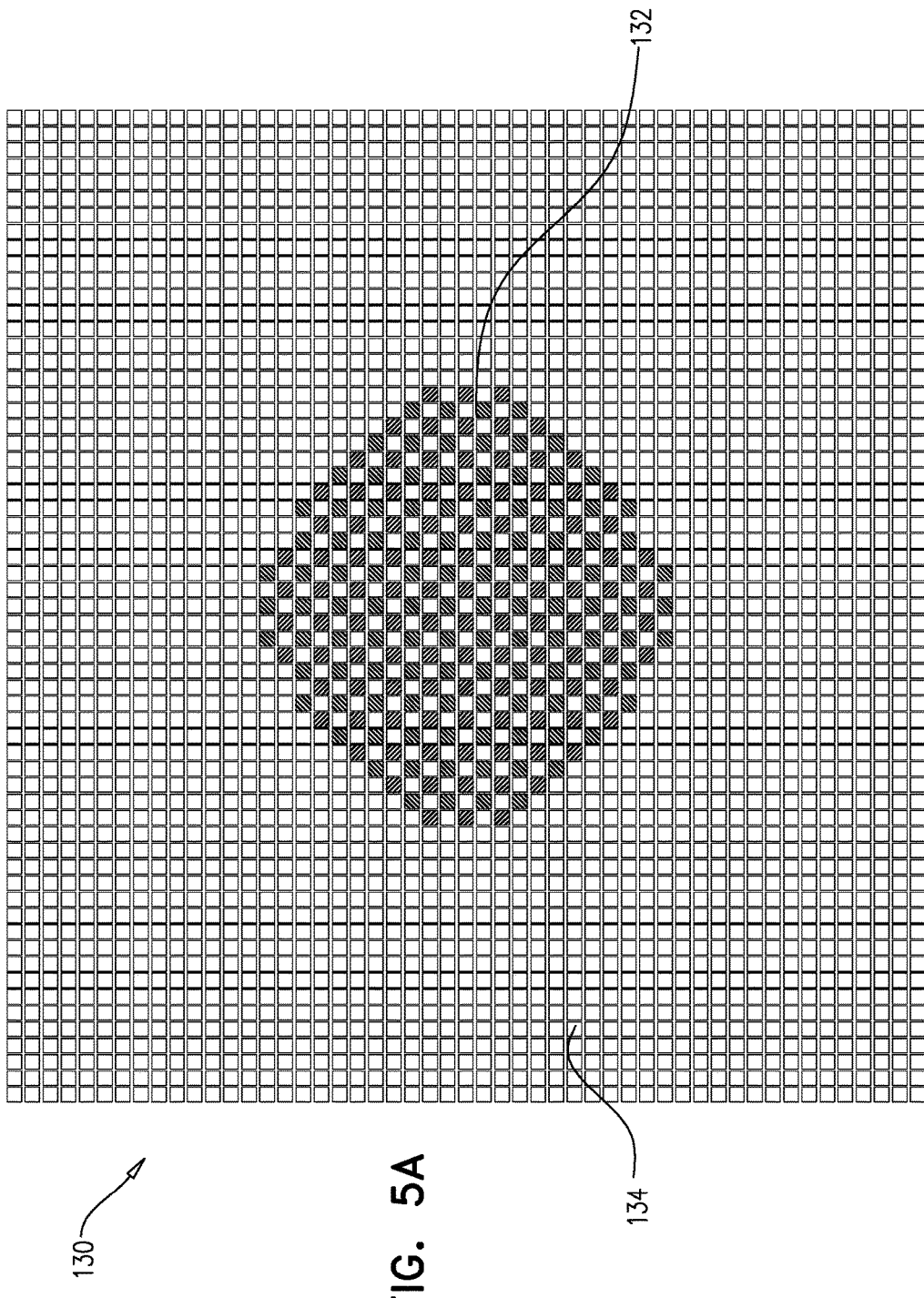
FIGS. 5A and. 5B are schematic illustrations of an intraocular display, in accordance with some applications of the present invention.
Figure 5B:
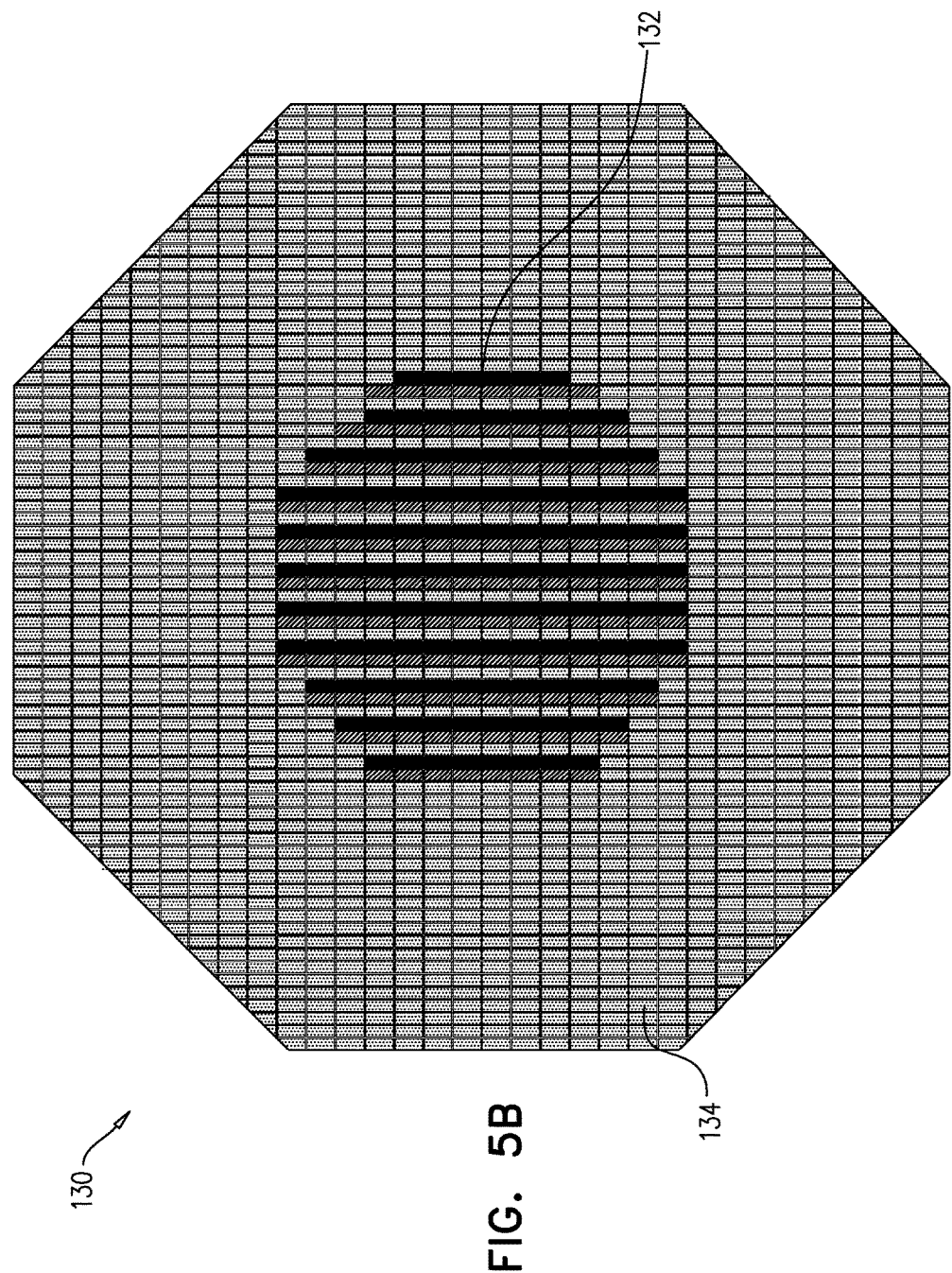

Reference is now made to FIGS. 5A-B, which are schematic illustrations of electronic display 130, e.g., a micro-LED display, in accordance with some applications of the present invention. Typically, display 130 has a central polychrome portion 132 and a peripheral monochrome portion 134, surrounding central portion 132. Central polychrome portion 132 is positioned to emit light which is projected onto a fovea of the retina. The fovea is an area in the retina having a large number of closely-packed cones, which are photoreceptor cells that are responsible for color vision. Central polychrome portion 132 has a diameter that is projected in and typically somewhat beyond the area of the fovea. Peripheral monochrome portion 134 is positioned to emit light which is projected onto the retina, generally outside of the fovea. Since a relatively small number of cones are disposed in the retina outside of the fovea, the use of a distinct monochrome portion 134 allows intraocular apparatus 30 to have better resolution in the peripheral portion, because color is only utilized in central polychrome portion 132. For some applications, data transfer requirements are reduced due to the use of color image data only with respect to central polychrome portion 132, and by reducing the pixel resolution in peripheral monochrome portion 134.

For some applications, electronic display 130 has a non-rectangular shape, e.g., a round shape or an octagonal shape, enabling better fit into a cylindrical encapsulation, and/or a closer match to an overall round shape of the healthy viewing field.

Reference is now made to FIG. 6 which includes a graph adapted from "Topography of the layer of rods and cones in the Kaman retina," Osterberg G., Acta Ophthalmol Suppl. 1935, 6:1-103, which is incorporated herein by reference. FIG. 6 shows electronic display 130, with respect to a fovea of the subject. As shown, central polychrome portion 132 projects onto the fovea where cone density is at a peak.

It will be appreciated by persons skilled in the art that the present invention s not limited to what has been particularly shown and described hereinabove. Rather, the scope of present invention includes both combinations and subcombinations of the various features described hereinabove, as well as variations and modifications thereof that are not in the prior art, which would occur to persons skilled in the art upon reading the foregoing description.

The invention claimed is:

1. Intraocular apparatus (i) shaped and sized to be implanted entirely in a subject's eye, (ii) having an anterior side and a posterior side, and (iii) configured for use with an extraocular imaging device, the intraocular apparatus comprising:
   a photovoltaic energy receiver on the anterior side of the intraocular apparatus configured to receive energy from outside the eye and to power the intraocular apparatus;
   a photodiode on the anterior side of the intraocular apparatus configured to receive data from the extraocular imaging device; and
   an application-specific-integrated-circuit (ASIC) on the posterior side of the intraocular apparatus comprising (i) circuitry configured to process the data from the photodiode into an image, (ii) an electronic display configured to emit light representing the image, and (iii) exactly three through-silicon vias connecting the ASIC to the photovoltaic energy receiver and to the photodiode.

2. The intraocular apparatus according to claim 1, further comprising a lens posterior to the ASIC, configured to focus the light emitted by the electronic display onto a retina of the subject.

3. The intraocular apparatus according to claim 1, wherein the intraocular apparatus is shaped and sized to be implanted in a capsular bag of the subject.

4. The intraocular apparatus according to claim 1, further comprising an encapsulation, at least partially comprising glass, the encapsulation configured to encapsulate the photovoltaic energy receiver, the photodiode, and the ASIC.

5. The intraocular apparatus according to claim 4, wherein a posterior side of the encapsulation forms a lens configured to focus the light emitted by the electronic display onto a retina of the subject.

6. The intraocular apparatus according to claim 1, wherein the electronic display comprises a light-emitting diode (LED) display.

7. Intraocular apparatus shaped and sized to be implanted entirely in a subject's eye and configured for use with an extraocular imaging device, the intraocular apparatus comprising: an electronic display comprising:
   a central polychrome portion; and
   a peripheral monochrome portion, surrounding the central portion,
   the electronic display being configured to emit light representing an image received by the imaging device.

8. The intraocular apparatus according to claim 7, wherein the electronic display comprises a light-emitting diode (LED) display.

9. Intraocular apparatus shaped and sized to be implanted entirely in a subject's eye and configured for use with an extraocular imaging device, the intraocular apparatus comprising: an electronic display comprising:
   a central portion; and
   a peripheral portion, surrounding the central portion,
   the peripheral portion having resolution that is higher than a resolution of the central portion.

10. The intraocular apparatus according to claim 9 wherein the electronic display comprises a light-emitting diode (LED) display.

11. The intraocular apparatus according to claim 9, wherein the central portion comprises a polychrome portion; and the peripheral portion comprises a monochrome portion.

* * * * *